United States Patent [19]

Doyle

[11] Patent Number: 4,758,088
[45] Date of Patent: Jul. 19, 1988

[54] MICROSCOPE ACCESSORY WHICH FACILITATES RADIATION TRANSMISSION MEASUREMENTS IN THE REFLECTANCE MODE

[75] Inventor: Walter M. Doyle, Laguna Beach, Calif.

[73] Assignee: Laser Precision Corporation, Utica, N.Y.

[21] Appl. No.: 45,368

[22] Filed: May 1, 1987

[51] Int. Cl.$^4$ .................. G01B 9/02; G01N 21/01
[52] U.S. Cl. .................. 356/346; 350/523; 350/527; 356/244; 356/440
[58] Field of Search ............... 356/244, 346, 432, 440; 350/523–528

[56] References Cited

U.S. PATENT DOCUMENTS 3,013,467 12/1961 Minsky .................. 356/432
4,191,940 3/1980 Polcyn et al. .................. 356/39 X

FOREIGN PATENT DOCUMENTS 1304134 8/1962 France .................. 350/527

Primary Examiner—Vincent P. McGraw
Attorney, Agent, or Firm—Thomas J. Plante

[57] ABSTRACT

A reflectance/transmittance structure is disclosed, which is adapted to be used in a microscope (primarily for infrared radiation) of a type disclosed in previous common inventor/common assignee applications. Radiation is passed through a Cassegrain objective lens on its way to the sample. It is reflected by a spherical mirror toward a flat mirror, then back to the spherical mirror, and then back through the sample on its way back to the Cassegrain objective lens. This arrangement permits retention of both the redundant aperturing and the injection mirror features of prior patent applications.

10 Claims, 5 Drawing Sheets

MICROSCOPE ACCESSORY WHICH FACILITATES RADIATION TRANSMISSION MEASUREMENTS IN THE REFLECTANCE MODE

BACKGROUND OF THE INVENTION

This invention relates to improvements in microscopes, and particularly to a microscope accessory which will permit measurement of radiation transmitted through a sample after reflection from a surface located on the side of the sample away from the objective lens.

As explained in common assignee/common inventor application Ser. No. 921,212, filed Oct. 20, 1986, it is highly advantageous to use reflectance microscopy in situations in which detector-received radiation is modulated by transmission through the sample. This use of the reflectance mode for transmission measurements conserves space in the microscope, and permits a single objective lens to transmit both pre-sample and post-sample radiation.

Another microscope improvement set forth in common assignee/common inventor application Ser. No. 921,066, filed Oct. 20, 1986, discloses the advantages of a "projected field stop" which provides a feature sometimes referred to a "redundant aperturing". This feature, which can be more accurately labeled "diffraction filtering" or "matched field illumination (MFI)", reduces diffraction effects in the microscope, and thus improves spatial resolution, by causing both pre-sample and post-sample radiation to pass through area-limiting field stops. The MFI effect provides definite benefits, particularly when it is necessary to distinguish between adjacent microscopic samples of two different materials.

Yet another microscope improvement set forth in common assignee/common inventor application Ser. No. 907,995, filed Sept. 16, 1986, discloses the advantages of high radiation throughput obtained in the microscope reflectance mode by using an "injection" mirror, which causes substantially 50% of the available IR beam to reach the detector.

SUMMARY OF THE INVENTION

The present invention provides an accessory which is both (a) usable in a microscope having the MFI and high throughput benefits discussed above, and (b) arranged to provide radiation transmission measurements in the reflectance mode.

The present invention enhances measurement sensitivity by causing the analytical radiation to pass twice through a microscopic sample. It utilizes two reflecting surfaces on the side of the sample away from the objective lens, one a curved surface, and the other a flat surface.

Because a single objective lens is used both for the incident and reflected radiation, the two fields-of-view are inherently coincident, thus simplifying alignment adjustments.

DETAILED DESCRIPTION OF SPECIFIC EMBODIMENTS

Figure 1:
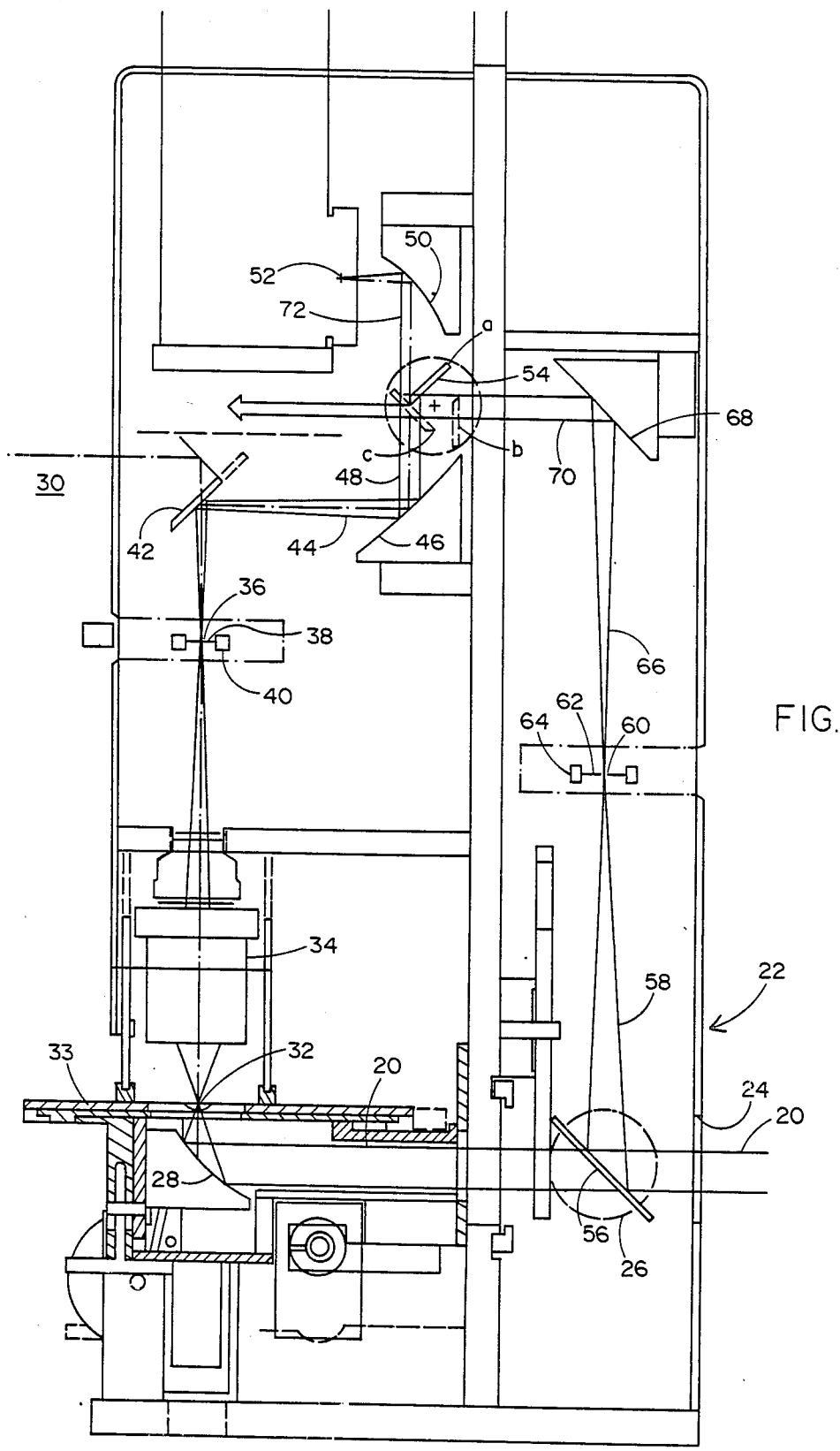
FIG. 1, which is substantially the same as FIG. 3 of U.S. Ser. No. 921,066, is a sideview of a microscope unit providing the environment into which the structure of the present invention may be incorporated.
Figure 3:
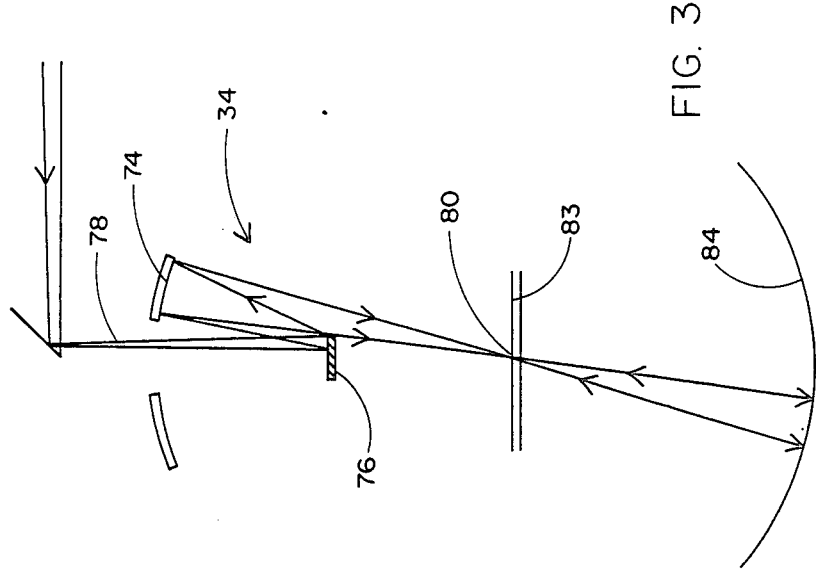
FIGS. 2 and 3 are schematics showing two alternative arrangements which would provide partial but not ideal, solutions of the problem which the present invention is intended to solve.

As indicated above, FIG. 1 essentially conforms to FIG. 3 of U.S. Ser. No. 921,066. It is described here in order to provide the background for clear understanding of the present invention.

A collimated radiation beam 20 enters the microscope housing 22 through an opening 24. An optical switching wheel, indicated by a dashed line 26, has various positions to accomodate various uses of the microscope. In the basic transmission mode, the wheel simply provides an aperture through which the collimated beam 20 passes directly to a parabolic mirror 28. For viewing through an eyepiece at 30, the incoming collimated radiation will be a collimated white, or visible, beam. For infrared anaylsis, the incoming radiation will be a collimated IR beam.

Parabolic mirror 28, which has a short focal length, causes the reflected beam 20 to focus at point 32, which is the sample location. The sample is supported in its focal plane on a platform, or stage, 33 which is position-adjustable under operator control in X, Y and Z axes, in order to bring the sample into the focal point. Mirror 28 is separately adjustable for alignment with beam 20.

After passing through the focal point 32, the diverging rays of the radiation beam enter a Cassegrain objective lens 34, which contains reflective surfaces for microscopic viewing of the sample. The focusing beam leaving objective lens 34 reaches its focal point at 36, which is in a focal plane 38 containing an adjustable stop (or iris) 40, the size of which is adjustable under operator control. A flat, movable view/test mirror 42 has three available positions. In one position, it permits visual inspection, and position-location, of the sample. In a second position, mirror 42 reflects infrared radiation which is transmitted through the microscope. In the infrared transmission mode, IR radiation from the interferometer, entering along path 20, follows the same path as that provided for visible radiation, until it is reflected by mirror 42 to provide diverging beam 44.

Beam 44 is recollimated by a parabolic mirror 46, and directed as beam 48 toward another parabolic mirror 50, which causes the radiation to focus at a detector 52. Note that a movable mirror 54, in this mode, must be in a position (position b) in which it does not block the collimated beam 48. Mirror 54 has a total of three available positions, two of which are reflecting positions, as will be explained below.

In one or more positions of mirror-carrying wheel 26, the entering collimated radiation will be reflected by a parabolic mirror 56 on the wheel, in order to provide focusing radiation 58 directed toward focal point 60. Focal point 60 is in a focal plane 62 containing another adjustable field stop (or iris) 64, the size of which is adjustable under operator control. After focusing at 60, a diverging radiation beam 66 will be reflected and recollimated by a parabolic mirror 68.

The radiation path between confocal paraboloids 56 and 68 is a radiation path separate from that of the radiation passing through objective lens 34. This separate path provides a plurality of advantages for the microscope unit, as discussed in U.S. Ser. Nos. 907,993 and 907,995. In U.S. Ser. No. 921,066, it provides another benefit, which is of vital importance. It permits the adjustable field stop 64 to control the field of view at the sample-located reflecting focal plane, with the advantages discussed in the latter application.

In the reflectance mode, collimated beam 70, reflected by mirror 68, will be partially reflected by movable mirror 54. This is a 100% reflective mirror, which has been moved to a postion in which it reflects half of beam 54 toward the Cassegrain lens 34 and the sample at 32. This 50% beam is caused by parabolic mirror 46 to focus at point 36 in focal plane 38, having been reflected toward that point by flat mirror 42, which has been moved into the appropriate position. This radiation will, as explained in detail in U.S. Ser. No. 907,995 pass downwardly through Cassegrain lens 34, be reflected by the sample at 32, pass upwardly through lens 34, and pass through focal point 36. It will then be reflected by flat mirror 42, and be recollimated by parabolic mirror 46 in the form of a 50% beam 72 which bypasses mirror 54, and reaches detector 52.

Note that the adjustable field stop 64 may be used to determine the size of the beam focused at the sample in the reflectance mode. Since the other adjustable field stop 40 is not initially used for this purpose, it can remain open sufficiently to avoid radiation back scatter resulting from reflection by the upper side of field stop 40. This also permits the focused center point to be viewed by the operator against a background of larger area, but less brightness (assuming visible background light is made available). Also, subsequent narrowing adjustment of field stop 40 provides the diffraction filtering, or matched field illumination (MFI), benefit discussed above.

Where, as in U.S. Ser. No. 921,212, it is desired to use the microscope for measuring a transmittance sample in the reflecting mode, the radiation will pass through Cassegrain 34 both as it approaches, and as it leaves, the sample. A simple approach would be that illustrated in FIG. 2. The Cassegrain objective lens 34 comprises a downwardly-reflecting larger mirror 74 and an upwardly-reflecting smaller mirror 76 located below the larger mirror. Radiation beam 78 enters the top of the Cassegrain, is reflected by mirror 76 to mirror 74, and is reflected by mirror 74 to focus at the sample 80. The sample 80 is supported on a fully reflecting platform surface 82, which causes reflected radiation to pass through the sample and then return through Cassegrain 34 toward the detector.

Figure 2:
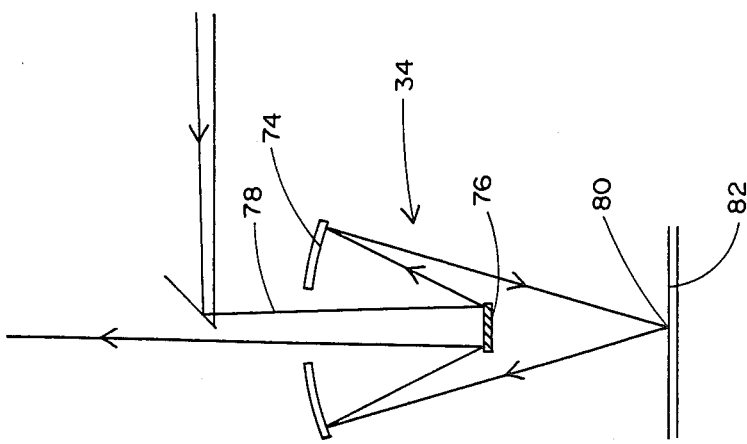

However, the arrangment shown in FIG. 2 has certain problems. First, in the case of very thin samples, it has been observed that anomalous results are often obtained when the sample is in contact with a reflecting surface. These effects are thought to be related to optical standing waves at the surface. Second, in the case of thick samples, or samples located on or in a thick substrate, it will be impossible to simultaneously focus the microscope on the sample and on the mirror, as must be done if both the incident and reflected optical paths are to be in focus.

FIG. 3 illustrates another possible approach. In this illustration, a spherical mirror 84 is placed below the sample 80, which is supported on a transparent platform, or window, 83. Radiation from the Cassegrain lens 34 will pass through the sample 80, be reflected by the mirror 84, and return through the sample toward the Cassegrain lens. This approach will work in a microscope employing a semitransparent beamsplitter, but not in one which uses field division of radiation, as described in U.S. Ser. No. 907,995. The reason for this is that the field division design uses one side of the Cassegrain aperture for incident radiation and the other side for reflected radiation. An incident ray which passes through the sample and is reflected by the spherical mirror will pass back through the sample and enter the same side of the objective lens that it emerged from. It thus will be blocked by the field division mirror, and will not reach the detector.

Figure 4:
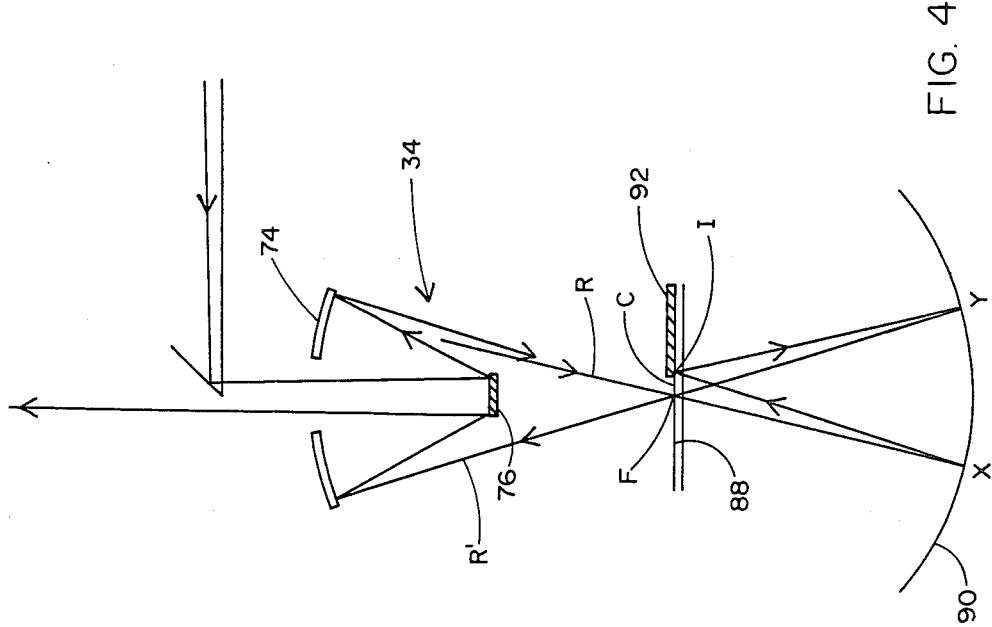
FIG. 4 is a schematic showing the preferred embodiment of the present invention.

The present invention solves the problems discussed above in a simple and elegant way, while providing the additional benefit of extremely simple adjustment. FIG. 4 shows the presently preferred embodiment. A sample is mounted on a transparent substrate, or window, 88, and is located at the focal point F of the microscope Cassegrain objective lens 34. A spherical mirror 90 is located below the window, with its center of curvature at the position C, which is nominally on the front surface of the window. A downward looking flat mirror 92 is mounted on the surface of the window adjacent to the sample location F. In practice, this can be either a separate mirror or a reflective coating deposited on the window. It can cover any area of the window except the area intended for sample viewing.

It can be seen from FIG. 4 that radiation passing through the sample at F will be reflected by the spherical mirror 90 to form a small image at I. As long as the distance CF is small compared to the radius of curvature of the spherical mirror, the image I will be approximately the same size as the original illuminated area, and the distance CI will be equal to CF. After striking the flat mirror at I, the radiation will be reflected back to the spherical mirror, and reimaged back at F where it will again pass through the sample. In other words, the radii of spherical mirror 90 which extend from the center of curvature C to points X and Y, respectively, on the circumference will each bisect the angles formed by the rays as they are reflected by the spherical mirror 90.

The device just described has two very important characteristics. First a ray, such as R, which is incident on the sample from one side of the Cassegrain, will return to the other side of the Cassegrain as R', after its second pass through the sample. This meets the requirement for use with the field division microscope of U.S. Ser. No. 907,995. Second, reimaging of the radiation at F is independent of the distance CF as long as it is small compared to the radius of curvature of the spherical mirror. In other words, this device has the very unique property of always reimaging a focus back on itself as long as both the original focus and the center of curvature are in the plane of the flat mirror. For a thin sample, these conditions are quite easy to achieve. The only critical dimension is the distance between the spherical mirror and the flat mirror. No lateral adjustments are needed.

Figure 5:
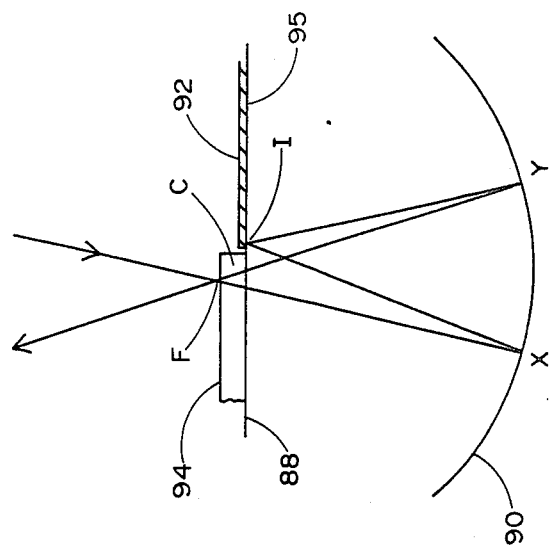
FIG. 5 is a schematic showing the embodiment of FIG. 4 after an adjustment has been made to accomodate a relatively thick sample.

For some situations, such as a microscopic impurity on or within a relatively thick sample, it will be desirable to provide the capability to adjust the distance between the spherical mirror 90 and flat mirror 92. This condition is shown in FIG. 5. In this case, optimum adjustment will occur when the center of curvature C is located midway between the sample plane 94 and the mirror plane 95 of the flat reflector 92 (after correcting for the indices of refraction of the various materials). The flat mirror 92 of this embodiment does not necessarily have to be at the surface of the window 88. It could be above the window, in which case a situation similar to that shown in FIG. 4 would occur.

Figure 6:
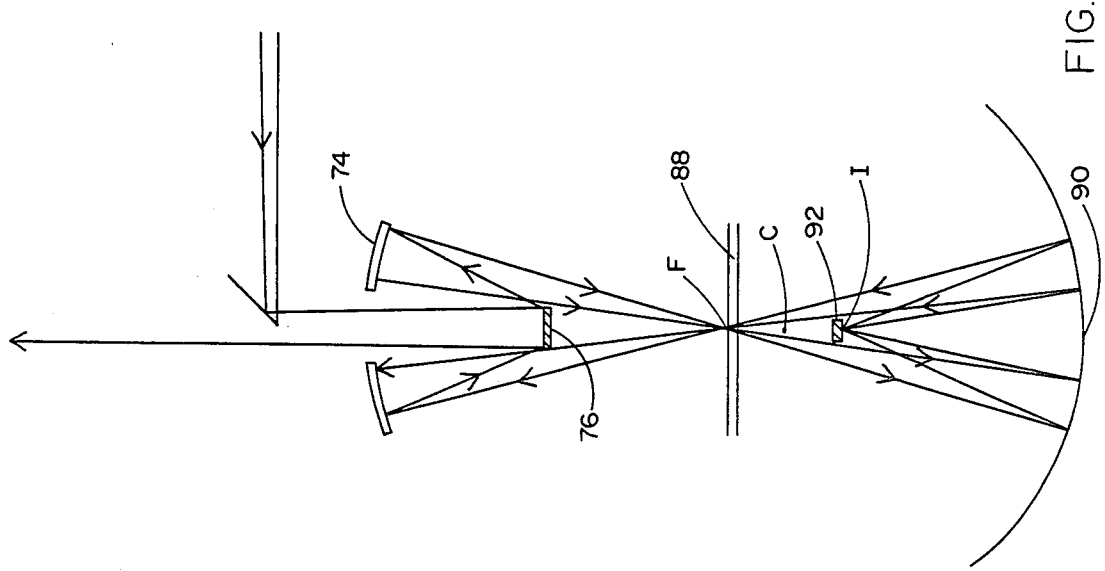
FIG. 6 is a schematic showing another embodiment of the invention.

Another embodiment of the invention is shown in FIG. 6. In this case, the flat mirror 92 is located below the sample-carrying substrate 88, and is in the shadow caused by the Cassegrain secondary mirror 76. This embodiment is not as flexible as the previous embodiment, in that the flat mirror must: (a) be completely within the shadow, but (b) must also not be too far from the sample plane, compared to the radius of curvature of the spherical mirror 90, so as to minimize spherical aberrations.

In both of the embodiments of FIGS. 4 and 6, the spherical mirrors could be replaced by elliptical mirrors with their two foci located at F and I. This would virtually eliminate aberrations when the mirrors are perfectly positioned, but would lead to very large abberations when either focus is displaced in any direction. The use of spherical mirrors is thus the preferred approach. It is only necessary to make sure that the radius of curvature of mirror 90 is sufficient to yield a blur circle (due to aberrations) which is small compared to the spatial resolution of the microscope. This requirement can be tested visually, since the aberrations will be the same in the visible and infrared for a reflecting optical system.

Figure 8:
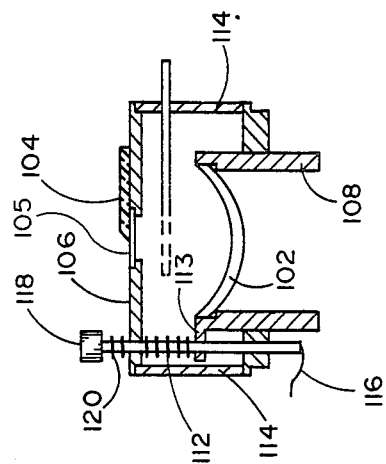
FIG. 8 is a closeup of the portion of FIG. 7 which incorporates the preferred embodiment of the invention.
Figure 7:
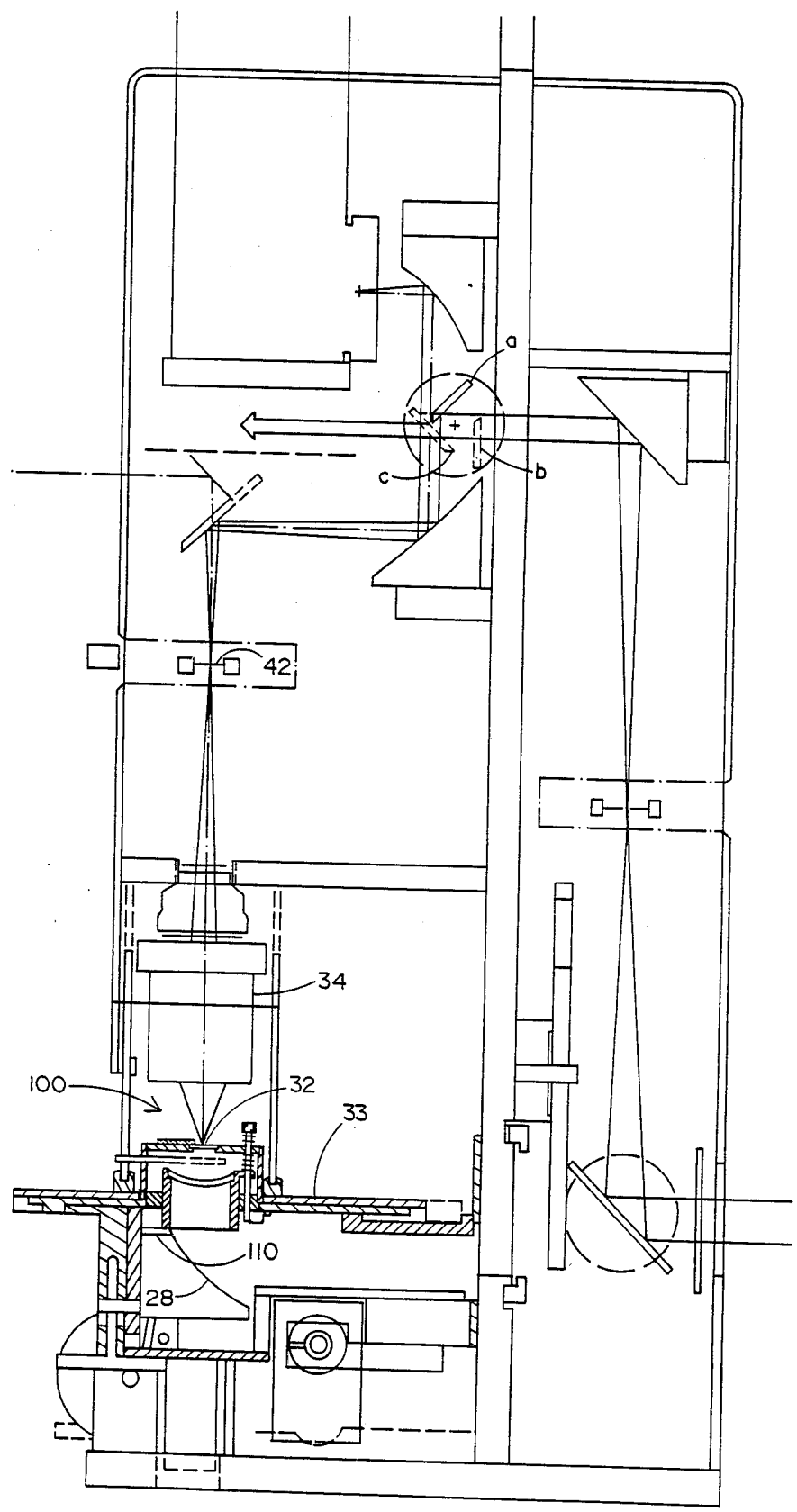
FIG. 7 is a sideview of a portion of the microscope unit of FIG. 1, into which an adjustable version of the structure embodying the present invention has been incorporated.

FIGS. 7 and 8 show details of a practical structure incorporating the invention, and also show how that structure may be incorporated into the microscope of FIG. 1. As shown in FIG. 7, without altering the other components of the microscope, a reflectance/transmitance structure (accessory) 100 which accomplishes the purposes of this invention, has been inserted into the microscope unit. The parabolic mirror 28 of FIG. 1 has been moved to its lowest position, in order to provide space for the reflectance/transmittance structure 100. The stage, or supporting platform, 33 has also been adjusted downwardly; and the added structure is on top of the stage 33, and is position—adjustable to locate focal point 32 by means of the adjustable stage.

The details of reflectance/transmittance structure 100 are shown more clearly in the enlarged view of FIG. 8. The mechanical details shown are merely exemplary, and may be altered to improve their functioning, except that a curved upwardly-facing concave reflecting surface 102 is required, and a flat downwardly-facing reflecting surface 104 is required. The reflecting surface 104 may be either a separate mirror, or a reflecting coating, e.g., aluminum, applied to the upper surface of sample-supporting window 105 (e.g., by vacuum deposition). The curved, preferably spherical, reflecting mirror 102 may conveniently be supported by a hollow cylindrical plunger 108, the lower edge of which rests on the upper flat body portion 110 of parabolic mirror 28 (see FIG. 7). A compression spring 112, which is between the lower surface of window holder 106 and an arm 113 extending from plunger 108, may be used to hold the accessory device in postion in the microscope. Vertical adjustment of paraboloid 28 may be used to adjust the vertical position of the curved mirror 102 relative to the position of the stage which carries both the sample and the flat reflecting surface 104.

A vertical supporting body 114 is provided, which is adapted to be positioned by the stage 33, and to be position-adjustable by movement with the adjustable stage. When the reflectance/transmittance structure has been inserted into the microscope, a retaining finger 116 may be moved, by turning a knob 118, into engagement with a surface 119 of the stage, against which it is urged by a compression spring 120 located between knob 118 and the upper surface of window holder 106.

As previously stated, the present invention provides a highly advantageous arrangement for obtaining sample analysis by means of a reflectance transmittance function. Some of the advantages of the reflectance/transmittance function were discussed in U.S. Ser. No. 921,212. However, in the structure disclosed in that application, the important diffraction-reduction advantage of matched field illumination had to be sacrificed. Also the structure of that application could not be readily inserted into the microscope unit shown in FIG. 1 of this application.

Matched field illumination reduces spectral contributions from undesired areas by reducing the illumination which occurs in these areas. When operated in the reflectance mode, the microscope disclosed herein allows matching of the diffraction pattern of the incident illumination with that of the microscope receiving optics, by using the same objective lens and field stop for both. Actually, the projected aperture, or field stop, 64 is used to define the illuminated area, rather than the received area, as is more conventional. However, it also allows the field stop immediately above the objective lens to be closed down to limit the received field, without incurring excess backscattering. It thus provides automatically aligned matched field illumination in the reflectance mode. The invention described in the current disclosure allows this benefit to be extended to the transmittance mode.

From the foregoing description, it will be apparent that the apparatus disclosed in this application will provide the significant functional benefits summarized in the introductory position of the specification.

The following claims are intended not only to cover the specific embodiments disclosed, but also to cover the inventive concepts explained herein with the maximum breadth and comprehensiveness permitted by the prior art.

What is claimed is:

1. In a microscope having sample supporting member which retains a sample in a sample focal plane, an objective lens, a detector to measure radiation which reaches the focal plane of the detector, and means for causing a post-interferometer radiation beam to enter the microscope, an optical system having a reflectance/transmittance mode function, comprising:
   a transparent sample-supporting member through which radiation passes after illuminating the sample;
   a curved concave reflecting surface which receives and reflects post-sample radiation back in the general direction of the sample;
   a flat reflecting surface which receives and reflects back the radiation reflected by the curved surface, in order to cause the latter to again reflect the radiation, causing it to illuminate the sample and continue in the direction of the objective lens.

2. The microscope of claim 1 in which:
the concave reflecting surface is spherical; and
the center of curvature of the concave reflecting surface is subtantially midway between the focal point of the objective lens at the sample and the point on the flat reflecting surface at which radiation from and to the concave surface is reflected.

3. The microscope of claim 1 which also comprises:
adjustable field stop means which determines the illuminated area at the sample and the area observed by the detector.

4. The microscope of claim 2 which also comprises:
adjustable field stop means which determines the illuminated area at the sample and the area observed by the detector.

5. The microscope of claim 3 in which both incoming radiation on its way to the objective lens, and radiation between the objective lens and the detector, pass through adjustable field stop means, in order to provide matched field illumination.

6. The microscope of claim 4 in which both incoming radiation on its way to the objective lens, and radiation between the objective lens and the detector, pass through the adjustable field stop means, in order to provide matched field illumination.

7. The microscope of claim 1 which also comprises:
a fully reflecting mirror which reflects approximately half of the incoming radiation toward the objective lens, and permits substantially the entire radiation returning from the objective lens to reach the detector.

8. The microscope of claim 3 which also comprises:
a fully reflecting mirror which reflects approximately half of the incoming radiation toward the objective lens, and permits substantially the entire radiation returning from the objective lens to reach the detector.

9. The microscope of claim 1 which also comprises:
an adjustable field stop through which the radiation passes both as it moves toward the sample, and as it moves from the sample toward the detector;
the adjustable field stop providing redundant aperturing for the purpose of reducing diffraction effects.

10. The microscope of claim 9 which also comprises:
another adjustable field stop through which incoming radiation passes as it moves toward the sample, but not as it moves from the sample toward the detector;
the adjustment of the latter field stop permitting back scatter from the other adjustable field stop to be minimized.

* * * * *